(12) United States Patent
Stack et al.

(10) Patent No.: US 9,439,592 B2
(45) Date of Patent: Sep. 13, 2016

(54) EYE TRACKING HEADSET AND SYSTEM FOR NEUROPSYCHOLOGICAL TESTING INCLUDING THE DETECTION OF BRAIN DAMAGE

(71) Applicant: Sync-Think, Inc., Boston, MA (US)

(72) Inventors: Matthew E. Stack, Boston, MA (US); Daniel J. Beeler, Jamaica Plain, MA (US)

(73) Assignee: SYNC-THINK, INC., Boston, MA (US)

( * ) Notice: Subject to any disclaimer, the term of this patent is extended or adjusted under 35 U.S.C. 154(b) by 0 days.

(21) Appl. No.: 14/685,473

(22) Filed: Apr. 13, 2015

(65) Prior Publication Data
US 2016/0038069 A1    Feb. 11, 2016

Related U.S. Application Data

(63) Continuation of application No. 13/506,840, filed on May 18, 2012, now Pat. No. 9,004,687.

(51) Int. Cl.
| A61B 3/14 | (2006.01) |
| A61B 5/16 | (2006.01) |
| A61B 3/113 | (2006.01) |
| A61B 5/00 | (2006.01) |

(52) U.S. Cl.
CPC ............... *A61B 5/162* (2013.01); *A61B 3/113* (2013.01); *A61B 5/6803* (2013.01)

(58) Field of Classification Search
CPC .............................. A61B 3/113; A61B 5/6803
USPC ................ 351/210, 209, 221, 246; 600/558; 345/7, 8; 359/630, 631, 633
See application file for complete search history.

(56) References Cited

U.S. PATENT DOCUMENTS

| 4,332,566 A | 6/1982 | Mazeski et al. |
| 4,407,299 A | 10/1983 | Culver |
| 4,838,681 A | 6/1989 | Pavlidis |

(Continued)

FOREIGN PATENT DOCUMENTS

EP    1 726 260    11/2006

OTHER PUBLICATIONS

Ball, "The Role of Higher-Order Motor Areas in Voluntary Movement as Revealed by High-Resolution EEG and fMRI," NeuroImage 10, 662-694 (1999), Article ID nimg.1999-0507, available online at http://www.idealibrary.com, 13 pgs.

(Continued)

*Primary Examiner* — Hung Dang
(74) *Attorney, Agent, or Firm* — Morgan, Lewis & Bockius LLP

(57) ABSTRACT

A universal headset-mounted Neuropsychological Testing System utilizes eye tracking, with a single screen fixed with respect to the face and a dot on the screen driven to present an object that both eyes are focused on using a set of prisms, with the prisms eliminating interocular distance considerations. Ultrathin optics cast a virtual image at 40 centimeters and a universal mask against which the test taker's face is placed fixes the single screen with respect to the face so that head movement is not a factor. Additionally, miniature cameras are located in the headset housing beneath the eyes, and a quick release tensioning unit provides easy headset mounting and removal. Moreover, all elements are located in the headset hood to eliminate the effects of head movement as well as environmental distractions.

16 Claims, 10 Drawing Sheets

(56) References Cited

U.S. PATENT DOCUMENTS

| | | | |
|---|---|---|---|
| 4,889,422 A | | 12/1989 | Pavlidis |
| 5,070,883 A | * | 12/1991 | Kasahara ............... F41G 3/225 351/209 |
| 5,137,027 A | | 8/1992 | Rosenfeld |
| 5,331,969 A | | 7/1994 | Silberstein |
| 5,491,492 A | | 2/1996 | Knapp et al. |
| 5,529,498 A | | 6/1996 | Cassily et al. |
| 5,649,061 A | | 7/1997 | Smyth |
| 5,662,117 A | | 9/1997 | Bittman |
| 5,743,744 A | | 4/1998 | Cassily et al. |
| 5,867,587 A | | 2/1999 | Aboutalib et al. |
| 5,942,954 A | | 8/1999 | Galiana et al. |
| 6,090,051 A | | 7/2000 | Marshall |
| 6,102,870 A | | 8/2000 | Edwards |
| 6,162,186 A | | 12/2000 | Scinto et al. |
| 6,231,187 B1 | | 5/2001 | Munoz et al. |
| 6,542,081 B2 | | 4/2003 | Torch |
| 6,575,902 B1 | | 6/2003 | Burton |
| 6,603,491 B2 | | 8/2003 | Lemelson et al. |
| 7,390,091 B2 | | 6/2008 | Clemons et al. |
| 9,072,481 B2 | | 7/2015 | Shelhamer |
| 2002/0099305 A1 | | 7/2002 | Fukushima et al. |
| 2003/0225342 A1 | | 12/2003 | Hong et al. |
| 2005/0177065 A1 | | 8/2005 | Ghajar |
| 2007/0236663 A1 | | 10/2007 | Waldorf et al. |
| 2010/0094161 A1 | | 4/2010 | Kiderman et al. |
| 2014/0327880 A1 | | 11/2014 | Kiderman et al. |
| 2016/0022137 A1 | | 1/2016 | Wetzel et al. |

OTHER PUBLICATIONS

Barnes, "Anticipatory Control of Hand and Eye Movements in Humans During Oculo-Manual Tracking," Journal of Physiology (2002), 539.1, The Physiological Society 2002, 14 pgs.

Chan, "Are There Sub-Types of Attentional Deficits in Patients with Persisting Post-Concussive Symptoms? A Cluster Analytical Study," Brain Injury, 2003, vol. 17, No. 2, 18 pgs.

EPO Office Action, App. No. 06813639.9, May 31, 2011, 11 pgs.

Gibbon, "Toward a Neurobiology of Temporal Cognition: Advances and Challenges, Current Opinion in Neurobiology," (1997) 7:170-184, 16 pgs.

Gredeback, "The Development of Two-Dimensional Tracking: A Longitudinal Study of Circular Pursuit," Exp. Brain Res. (2005) 163:204-213, 10 pgs.

Green, "Deficits in Facial Emotion Perception in Adults with Recent Traumatic Brain Injury," Neuropsychologia, (2004) 42:133-141, 9 pgs.

Ghajar, International Search Report, PCT/US2006/032773, Jan. 22, 2007, 14 pgs.

Hulsmann, "From Will to Action: Sequential Cerebellar Contributions to Voluntary Movement," NeuroImage, (2003) 20:1485-1492, 18 pgs.

Kathmann, "Deficits in Gain of Smooth Pursuit Eye Movements in Schizophrenia and Affective Disorder Patients and Their Unaffected Relatives," Am J. Psychiatry 160:4, Apr. 2003, 8 pgs.

Lewine, "Neuromagnetic Assessment of Pathophysiologic Brain Activity Induced by Minor Head Trauma," AJNR Am. J. Neuroradiol., (May 1999) 20:857-866, 10 pgs.

Lutz, "Guiding the Study of Brain Dynamics by Using First-Person Data: Synchrony Patterns Correlate with Ongoing Conscious States During a Simple Visual Task," PNAS, (Feb. 5, 2002) 99(3):1586-1591, 6 pgs.

Madelain, "Effects of Learning on Smooth Pursuit During Transient Disappearance of a Visual Target," J. Neurophysiol., (2003) 90:972-982, 11 pgs.

Mangels, "Effects of Divided Attention on Episodic Memory in Chronic Traumatic Brain Injury: A Function of Severity and Strategy," Neuropsychologia, (2002) 40:2369-2385, 17 pgs.

Mehta, "Forward Models in Visuomotor Control," J. Neurophysiol., (2002) 88:942-953, 12 pgs.

Pedersen, "Origin of Human Motor Readiness Field Linked to Left Middle Frontal Gyrus by MEG and PET," NeuroImage 8, 214-220 (1998), Article No. NI980362, 7 pgs.

Perbal, "Relationships Between Time Estimation, Memory, Attention, and Processing Speed in Patients with Severe Traumatic Brain Injury," Neuropsychologia, (2003) 41:1599-1610, 13 pgs.

Smith, "A Right Hemispheric Frontocerebellar Network for Time Discrimination of Several Hundreds of Milliseconds," NeuroImage, (2003) 20:344-350, 7 pgs.

Strauss, "Intraindividual Variability in Cognitive Performance in Three Groups of Older Adults: Cross-Domain Links to Physical Status and Self-Perceived Affect and Beliefs," Journal of the International Neuropsychological Society (2002), 8, 893-906, 14 pgs.

Cronin-Golomb, et al., "Visual dysfunction in Alzheimer's disease: relation to normal aging," Annals of neurology 29.1 (1991): 41-52.

Sync-Think, Inc., International Preliminary Report on Patentability, PCT/US2014/050774, Feb. 16, 2016, 9 pgs.

Sync-Think, Inc., Communication Pursuant to Rules 161(1) and 162, EP14755513.0, Mar. 23, 2016, 2 pgs.

\* cited by examiner

EYE TRACKING HEADSET AND SYSTEM FOR NEUROPSYCHOLOGICAL TESTING INCLUDING THE DETECTION OF BRAIN DAMAGE

RELATED APPLICATION

This is a continuation of U.S. application Ser. No. 13/506,840, filed May 18, 2012, now U.S. Pat. No. 9,004,687, which is incorporated herein by reference in its entirety.

FIELD OF THE INVENTION

This invention relates to neuropsychological testing and more particularly to an eye tracking headset and system for providing reliable neuropsychological testing results.

BACKGROUND OF THE INVENTION

In the field of neuropsychology there have been numerous tests primarily designed to detect reaction time of individuals to certain stimuli. These tests have been used to detect brain damage in terms of motor skills and cognitive ability, by measuring an individual's reaction time when having to make a decision.

The questions on which the decision is to be made are oftentimes formulated in terms of displaying certain indicia to which the individual is asked to react. Thus, for instance, an individual may be presented with a red sphere or a green sphere and is asked to make a decision based on whether he perceives this sphere to be red or green. These and related reaction time tests are relatively straightforward and are limited in what they measure. As a result, the tests are given to the patients many times, and then reaction time scores are averaged together, in order to arrive at a single score, or some other metric is applied to compress the scores into a single number.

As mentioned above, cognitive impairment has been measured using reaction time tests. However, there are only a handful of tests that involve reaction time to test either cognitive performance or impairment, or both. Performance and impairment are at two ends of the spectrum. It is the goal of some of today's reaction time tests to allow one to decide when an impaired state exists, what the impaired state is, and what constitutes a higher state of performance in the cognitive sense.

The problem with reaction time tests is that when the individual is taking a stimulant, or a muscle relaxer of any type, this affects muscle response and therefore reaction time. Moreover, one of the major problems with reaction time tests is the variability of test retest accuracy. In reaction time tests one is measuring events at a rate of 200 to 400 milliseconds. However, the error rate is often at or in excess of +1-100 milliseconds from test to test. In order to eliminate the problem of error rate, these tests are performed repeatedly, with averages taken in order to obtain a response baseline. It will be appreciated that obtaining such a baseline is very difficult, and is especially difficult given a sequence of perhaps hundreds of little tests.

Aside from the ability to recognize and respond quickly to the recognition of objects, a recently highly studied measurement of cognitive involves what is known as the blink test in which the subject performs what is known in the field of neuropsychology as an attentional blink. The attentional blink occurs when a human patient or test subject is asked to make choices about what is presented on-screen. When the individual is presented with a choice to be made that he or she is supposed to log or memorize, a so-called blink indicates that the individual understands that there is a decision to be made and is saving this information in memory. The blink is not necessarily a blink in terms of closing one's eyes but is called an attentional blink because the individual can no longer absorb any information while staring at a screen for a short period after being exposed to the information they are supposed to memorize or react to. The attentional blink phenomenon is an example of an artifact of the brain that involves memory, attention, and reaction, and is heavily studied. Despite the large number of research papers and studies examining the attentional blink, few if any of these have produced fruitful results or insight about cognitive performance. Furthermore, the phenomenon is so short in duration, and methods of determining whether a person has expressed the phenomenon are so high level, that there is very little precision. Thus to date very little information is extracted from this form of cognitive testing. In practice today, attentional blink responses are measured by presenting an individual with a series of letters and numbers and then determining which letter or number the individual cannot remember immediately after a special target symbol is displayed.

Aside from reaction times, cognitive function is also measured utilizing technologies and methods that examine the movement of the eyes in relation to a displayed or projected test. Eye tracking cognitive testing is designed specifically to track the eye while it follows a moving dot. The ability of the eye to track the dot as the dot moves yields a measure of cognitive ability. It has been found that a technique called smooth pursuit eye tracking can be used to diagnose cognitive function by measuring small variations in the smooth pursuit data. These variations are quite small and it is only with much calibration and the blocking out of environmental effects that one can see these variations at all. How to reliably measure these small variations is the problem to be solved.

By way of further background, the type of dot moved in neuropsychological testing involves moving dots on a screen in a linear fashion followed by tracking the gaze direction of the eyes. Thus, these dots were moved in an X direction and a Y direction. When the dot was moved from one extreme to the other, the eye begins to flicker because the eye loses track of the dot. A flicker at the extremes of the eye's motion, indicates a loss of tracking the dot, and thus some cognitive limit or change in function, possibly impairment. Although all humans, including non-impaired patients, tend to exhibit some degree of jitter or flicker at the extremities of looking to the left or right, or up or down, the nature of the jitter is thought to express some underlying characteristic of cognitive performance.

Regardless of the type of flicker test, it was thought that predictable brain trauma could be ascertained by eye tracking involving horizontal x axis movement versus y axis movement of a dot. These x, y dot movement tests could be predictive of not only brain trauma, but also some other type of trauma other than traumatic brain injury, or TBI.

The major problem with the translation of a dot either in the x direction or in the y direction is that when one seeks to detect eye motion responsive to following a moving dot, one in fact detects eye movement at the fringes, i.e. at the extreme positions of the eye. Detecting data from the fringes is unreliable because both the data and flickering eye are erratic. Thus, it is necessary to cancel out the effects at the fringes in order to get a continuous sequence of data in the middle that is useful in determining cognitive ability. If one can obtain a continuous sequence of data this permits detection of variations in eye tracking ability using more advanced and yet more reliable mathematical constructs, such as variability, aggregation, and standard deviation to name a few. If the dot movement is detected not at extremes but between them, this is referred to as smooth eye tracking.

Thus, what is required for sensitive measurement of cognitive ability is continuous sequences of data from smooth eye pursuit in order to sensitively detect cognitive ability due to variations in the ability of the eye to track. To detect cognitive impairment one looks at the variability with which the eyes track an onscreen object. It is only by taking the smooth transition of the eye as it tracks the object that one is able to obtain predictable smooth movement variations.

Once one is able to detect the predictable smooth movement increments, one can measure cognitive impairment based on the measurement of the continuous sequence of data in terms of variability of the eye to track the on-screen image. It is the variability of the smooth eye pursuit that is indicative of cognitive function. How to obtain these variability increments so as to detect minute variabilities is a problem with current techniques, and requires time consuming calibration as will be discussed.

As to measurements of variability there are a number of techniques, for instance measuring the amount by which the eye is ahead of the moving dot, behind a moving dot, or on top of the moving dot. These measurements ascertain the amount ahead, behind or on top throughout the entire test and more importantly the variability of the movement.

As described above, these types of tests are one called smooth pursuit tests and the area of interest is called smooth pursuit eye tracking. The purpose of this type of testing is to provide consistent data in a sequential data set from the start of the test until the end of the test in which the data points considered are not interrupted by the edge effect of the eye going back and forth, and thereby introducing jitter or flickering movements of the eye sometimes referred in the art as saccading, which are both difficult to analyze mathematically, and difficult to replicate with precision from one test to another.

Moreover, a further caveat to any eye tracking test is that the tests is affected by actual eye blinking. It will be appreciated that with one or two eyes blinks, data is dropped during the duration of the blink, and often for some period slightly before and after the blink, as the eyelid obscures the portion of the eye that is being measured by the smooth pursuit eye tracking technology. In order to accommodate blinking when eye blinking is detected, the data is ignored during any analytical stage.

The above describes a dot that moves in a straight line from one end to the other and then reverses itself. It has been found that by moving the dot that the eye is focusing on in a circle, one does not have to artificially carve off the effects of the edges as the eye abruptly changes direction at the end of a linear sweep. As a result, circular movement is a more natural way of aggregating data to variability algorithms.

In order to measure the smooth eye pursuit, various eye tracking methodologies have been used. Researchers have been tempted to use virtual reality head mounted displays because of their availability but the results are not satisfactory. While a number of virtual reality head mounted displays exist, no virtual reality headsets are used for eye tracking primarily because they provide binocular 3D virtual reality viewing that requires calibration of the binocular channels. It also has to take into account intraocular distance so as to calibrate one eye with the other when 3D virtual reality headsets having two separate screens are used, which makes sensitive measurements virtually impossible.

As will be appreciated, these virtual reality headsets provide an individual with a set of screens in front of his eyes that are viewed in binocular fashion. To the extent that virtual reality headsets have been used for neuropsychological testing, these screens are utilized not for eye tracking but rather to present images to the individual and the individual is provided with clickers to measure reaction time. The reason that these head mounted displays are utilized for reaction time testing is that they provide a controlled environment that cancels outside noise and distractions when administering a test. Thus the utilization of virtual reality head mounted displays provide a controlled way of administrating reaction time tests, but to date they have not been utilized for eye tracking.

One of the reasons that they have not been adopted for eye tracking is the aforementioned binocular affect, which must be compensated for if one is utilizing the two screens to present an image to be tracked. Using the two screens requires a large amount of calibration because each of the eyes is focused on a different screen, measurements must be calibrated for interocular distance, and the present virtual reality headsets do not have a wide enough field of view for certain types of neuropsychological tests, such as circular smooth pursuit. Thus, virtual reality systems are not in general applicable to eye tracking.

As a result eye tracking usually involves a desktop-mounted system. This can involve the use of an infrared light source arranged on the desktop or nearby surface; or some sort of an optical infrared camera as used that sits on the desk and looks back up at the eyes as the individual's eyes track an image. Aside from calibration, head movement during the test and the effect of outside stimuli and environmentally induced artifacts affect test results.

Another classic system is one in which a tracking device is mounted directly on the eye itself and the eye looks through a translucent piece of semi transparent material. Infrared light is then directed towards the eye, with reflections captured on a camera that looks through the transparent material at the pupil. In this type of system there is no screen associated with the eye tracker. Instead, the screen is placed externally for instance on a monitor on a desk that a subject must look at.

A third type of system places dots on a screen and monitors eye movement of an individual viewing the screen. However, head movement is a very large problem. It is a false assumption that those taking the test can keep their heads still. This is especially true with individuals with cognitive impairment who are often times trying to move their head around. As the individual moves his head around and the individual is staring at a screen, if they move their head to the right the eye tracker data drifts because it does not account for head location. Thus, the eye tracker cannot track where the individual is looking because the individual's eyes can still follow the test dot over the screen even though the head is moving. Therefore, one of the major problems is that one has to fix the location of the screen with respect to the head or one has to exactly track the position of the head in real time.

The fourth category for eye tracking involves fixing the head to a mount and placing dots, stickers, or similar types of markers on the face, head, or body to decide where the head is looking. These systems then place an eye tracker close to the eye and ask a patient to look at a screen. Systems like this are used when head direction and eye detection must be determined in environments that might be inaccessible to traditional mechanical solutions. For example, this technology is currently used inside CAT scan machines, fMRI machines, EEG machines and MEG machines. In order to measure brain damage these systems use functional magnetic resonance imaging, or fMRI, that looks inside the brain to see the activity of the brain and what parts of the brain are illuminating responsive to the test stimuli. As an fMRI test is performed, the technician is asking the patient to track on certain images, all of which leads to a fairly complicated system for pinpointing the reaction of the brain to the eye tracking of an on-screen image. A further problem in EEG imaging is the ability to accommodate blinking. When a patient blinks he creates a massive electrical disturbance inside the brain that oftentimes overruns the EEG imaging machine so that all of a sudden the signal data that is being accumulated does not effectively track what one is thinking because what one is thinking is completely perturbed by the blink. This introduces an artifact which disrupts the entire signal obtained during eye tracking. Therefore, one of the problems involved with these types of eye movement detection systems is the requirement to fix the screen with respect to the eye and to provide a controlled environment.

In order to do this, those involved in the industry attempt to detect head direction by placing beacons on the head, which in one embodiment involves a cap of dots or set of dots that are detectable. Alternatively, infrared reflectors are placed on the head with their location detected by infrared cameras. These head position detectors are then utilized to cancel out the affect of drift as one's head is looking left and right or up and down toward the screen. More recently, the advancement of infrared based 3D positioning technologies has led some to hypothesize the feasibility of using infrared and/or other optical technologies to detect the surface of the head, and thereby induce the direction the head is pointing. Today, the precision of these head direction detection technologies is insufficient to provide the precision required by cognitive testing via analysis of the position of the eyes. In practice, the errors introduced in detecting the head's x, y, z position and direction overwhelm and greatly exceed the eye-based and optical measurement precision, so they typically do more harm than good. The problem with all of these systems is that they do not work because the error in detecting which way the head is facing ends up vastly overwhelming the measurement of the eyes. Thus if one is attempting to measure smooth pursuit eye motion variability, this small variability is lost.

Remote Gaze Estimation

Eye tracking involves remote gaze estimation. Assuming an immobilized head, one can perform a corneal reflective eye tracking procedure by maintaining a stationary object that reflects off the eye and then determines where that stationary object is if it moves on the eye pupil surface. Having determined this movement, one can calculate a ray directly back to the screen to calculate gaze position, as opposed to eye pupil position.

The general theory of remote gaze estimation utilizing the pupil center and corneal reflections is described by Elias Daniel Guestrin and Moshe Eizenman in the IEEE Transactions and Biomedical Engineering Volume 53 column 6, June 2006 in which the general theory for the remote estimation of the point-of-gaze from the coordinates of the centers of the pupil and the corneal reflections are discussed. The corneal reflections are produced by light sources that illuminate the eye, and the centers of the pupil and the corneal reflections are estimated in video images from one or more cameras. When using one camera and one light source the point-of-gaze can be estimated only if the head is completely stationary. However, attempts have been made to cancel out the movement of the head by using one camera and multiple light sources, where the point of gaze is estimated with free head movements following the completion of a multiple-point calibration procedure. Experimental and stimulation results are said to suggest that the main sources of gaze estimation are the discrepancy between the shape of real corneas and the spherical corneal shape assumed in the general theory. Moreover, errors occur because of the noise in the estimation of the centers of the pupil and the corneal reflections.

In a book by T. Ohno, K. Hara, and H. Inagaki in a chapter entitled "Why is personal calibration required?", it is said that in the majority of cases no tracking system can estimate the gaze direction accurately without personal calibration, also saying that many factors trigger gaze measurement error. The main causes of gaze measurement error are said to be the personal difference in eye ball size and shape which among adults involves a ten percent difference in eyeball radius and secondly the refraction at the corneal surface. Note, one considers the refraction at the corneal surface because the region between the cornea and crystalline lens is filled with a fluid called the aqueous humor. Because of the fluid, the observed pupil differs from the real position so that the calculated gaze contains some measurement error.

There is also a difference between the optical axis and the visual axis. The optical axis is defined by the center of the pupil and the center of the corneal curvature. This, however, differs from the eye gaze, which is called the visual axis. The visual axis is defined as the vector from the fovea, the highest resolution area on the retina, to the center of the crystalline lens. Since it is difficult to observe the exact position of the fovea by any of the cameras likely to be used in the gaze tracking system, the visual axis cannot be determined. To calculate the visual axis from the optical axis, it is necessary to compensate for this difference.

Another problem involved in calibration is the screen difference. If the size, the position, and the resolution of the computer screen are not fixed, it is not possible to determine the gaze position on the computer screen. In this case, it is necessary to display several calibration markers on the screen for estimating the parameters related to the computer screen. The presence of unknown parameters generally increases the number of calibration markers needed.

As mentioned above, there is the problem of eye positioning error which is introduced when the gaze tracking system allows free head movement. It is to be noted that the user's eye position is generally different from the initial position used for personal calibration, because the head drifts in the x, y, and z direction during the administration of the test. This often causes gaze measurement error because the gaze tracking parameters differ from the initial calibration condition.

Finally, there is the problem of refraction at the surface of eyeglasses, contact lenses, or other corrective or optical enhancement technologies. When the user wears eyeglasses or contacts, refraction appears at the surface of the glasses. It is necessary to consider that observed pupil position and its size are different from the real ones if the gaze tracking system user wears corrective eye wear.

As mentioned above, existing personal calibration measures include a calibration-free gaze tracking method in which multiple cameras and multiple point light sources are used to estimate gaze direction. Morimoto et al. propose another calibration-free gaze tracking method which utilizes at least one camera and two or more infrared light sources. The accuracy is determined utilizing simulated synthetic eye images in terms of viewing angle, whereas the difference between visual axis and the estimated gaze direction is not considered.

There is however a two point calibration gaze tracking method in which the basic idea of the proposed gaze tracking method is to reconstruct the user's eyeball position. The gaze direction is then estimated in a 3-D coordinate system with residual errors compensated by personal calibration.

Finally, there is a technique for determining eye position using stereo cameras. The first step in this system of gaze tracking is determining the eye position by the eye positioning unit, utilizing a stereo vision technique. The eye positioning unit uses a stereo camera which is calibrated by Tsai's camera calibration algorithm that utilizes the camera's intrinsic parameters including focal length, radial lens distortion and the principal point i.e. the intersection of the camera's Z axis and the camera's charge coupled device (CCD) image plane. Also included in the algorithm are extrinsic parameters including translation and rotation parameters which are used to permit transformation between the world and the camera coordinates. With these parameters, an object in the image coordinates can be transformed into a point in world coordinates when the distance between the camera and the object is given.

To calculate the user's 3-D eye position, the eye positioning unit first detects the user's eye in each camera image by image processing. The distance between the camera and the eye is then derived from the stereo image. Next, the eye position in world coordinates is calculated from the distance between the camera and the eye. There the eye position in the bitmap image taken by the camera is determined.

What can be seen from the above, is that present techniques for estimating gaze direction are fraught with calibration requirements. What is therefore needed is the ability to accurately sense the gaze direction so as to be able to measure smooth pursuit eye tracking results without time consuming calibration techniques, yet still maintaining a high level of accuracy and precision.

SUMMARY OF INVENTION

At the outset, in the subject system what is measured is anticipatory timing in terms of the anticipation as the eye of the subject anticipates where a moving dot will be as it is moved. This anticipation is measured as lag time for the eye to track the dot.

For normal individuals there will be a regular amount of anticipation or lag time from one dot position to the next. On the other hand, with impairment the eye jumps ahead and waits for the dot to catch up. Thus the lag time between dot movements varies. Measurement of the variability of anticipation is indeed difficult due to distractions from the environment and calibration issues having to do with the exact position of the screen on which the dot is presented with respect to an eye, and the synchronization between what each eye sees as well as interocular distance.

The subject headset mounted system addresses these issues to provide robust anticipation variability measurements.

While the above techniques are vastly over engineered and use hardware to try to solve an optical system problem, a much simpler system is simply to fix the screen with respect to the face, find a way to put cameras near the face in a stable position, and use optics involving prisms to allow each eye to look at the same dot on a screen in an enclosed contained environment.

In the subject invention a universal headset-mounted system is employed for rapid and accurate neuropsychological testing without calibration. The headset carries a number of components including a screen at the front of a hood, prisms and ultra thin lenses ahead of a universal mask gasket, light sources for corneal reflection, cameras underneath the eyes to ascertain gaze direction from corneal reflections, headset-mounted electronics and a quick release headset-mounting and tensioning system. All of the above permits rapid and sensitive neuropsychological testing.

More particularly, the headset carries only one screen and prisms in front of the eyes that bend the light so that both eyes are focused on the same dot on the single screen.

Secondly, the screen is immobilized at a fixed position with respect to the eyes using a specialized mounting system that involves a universal mask against which the test taker places their face and forehead.

As mentioned above, miniature cameras are located within the headset housing looking up at each eye, in which the field of view of the cameras is not blocked by the universal mask.

Moreover, the headset is secured to the head using a quick release tensioning unit that employs a unique strap and wire tensioning system for quick mounting and release.

Also, a set of thin lenses allows one to cast a virtual image at about 40 centimeters, with 40 centimeters being a natural gazing position since one can read text very easily at 40 centimeters. Thus the thin lenses are utilized to place the virtual image at 40 centimeters. 40 centimeters is not to be interpreted as a precise number, but a destination figure, plus or minus 10%. Thus the 40 centimeters is selected because it is roughly the distance at which anyone, whether needing corrective optics such as glasses, contact lenses or corrective surgery can still see an image without blurring.

Not only does this head-mounted system eliminate head movements as a factor, the headset eliminates extraneous noise and distractions from the environment.

The result is that there is no calibration necessary and tests can be run in as little as 3 minutes start-to-finish. By comparison, other current and pre-existing calibration systems require up to 30 minutes, and sometimes longer, to initialize, conduct, and complete the calibration process.

Thus, in a preferred embodiment, a single screen is mounted to an adjustable one size fits all headset to provide an enclosed head mounted display such that the single screen is carried by the headset and is precisely positioned ahead of the individual's eyes. The headset has a precision soft firm mask that rests on the individual's forehead, cheeks and chin to keep the individual's eyes at a fixed location relative to the screen. Note the enclosed head mounted display cancels out the effects of the environment to in essence place a black box in front of the eyes, thus eliminating distractions.

Rather than providing the two screens of a virtual reality headset, only one screen is used. The screen is viewed by the two eyes of the individual through prisms such that the dot on the screen that each eye is looking at is the same due to the convergence or light bending afforded by the prisms. As a result, binocular viewing is collapsed to monocular viewing, eliminating any alignment or synchronization problems that would occur if one were using the two screens common in virtual reality headsets to give 3-D depth viewing. Here viewing depth is avoided. Also the prisms cancel out the effect of interocular distance variation. The net effect is that one does not have to coordinate the images on the two screens. As a result, one does not have to do any of the eye tracking calibration associated with stereoscopic artifacts of eye tracking.

Note that in one embodiment thin rounded prisms are placed in front of the thin lenses so as not to disturb the optimal 40 centimeter distance.

More particularly, while utilizing two screens is not important in tests involving reaction time, it is extremely important not to use two screens when one is studying fine tracking movements of the eyeball. This is because if for whatever reason the two images are out of synchronization, the person viewing the object sees two objects and the brain begins to merge these objects; or the individual has difficulty seeing the object at all. This introduces effects like stereoscopic artifacts that make the ball appear to drift in the $3^{rd}$ dimension towards or away from the face.

Therefore, the purpose of the prisms is to present a single dot, not two dots, to eliminate any kind of asynchrony and so as not to have to account for interocular distance.

If one were to use the virtual reality headsets mentioned above, calibration takes as much as a half an hour and involves a person sitting down to do the 5 or 9 "dot plot" test where the individual has to look at dot number 1 or dot number 4, etc. Thus the subject system eliminates all of the problems associated with binocular viewing.

In summary, a universal headset-mounted Neuropsychological Testing System utilizes eye tracking, with a single screen fixed with respect to the face and a dot on the screen driven to present an object that both eyes are focused on using a set of prisms, with the prisms eliminating interocular distance considerations. Ultrathin optics cast a virtual image at 40 centimeters and a universal mask against which the test taker's face is placed fixes the single screen with respect to the face so that head movement is not a factor. Additionally, miniature cameras are located in the headset housing beneath the eyes, and a quick release tensioning unit provides easy headset mounting and removal.

Moreover, all elements are located in the headset hood to eliminate the effects of head movement as well as environmental distractions.

BRIEF DESCRIPTIONS OF THE DRAWINGS

These and other features of the subject invention will be better understood in connection with the detailed description in conjunction with the drawings of which:

Figure 4:
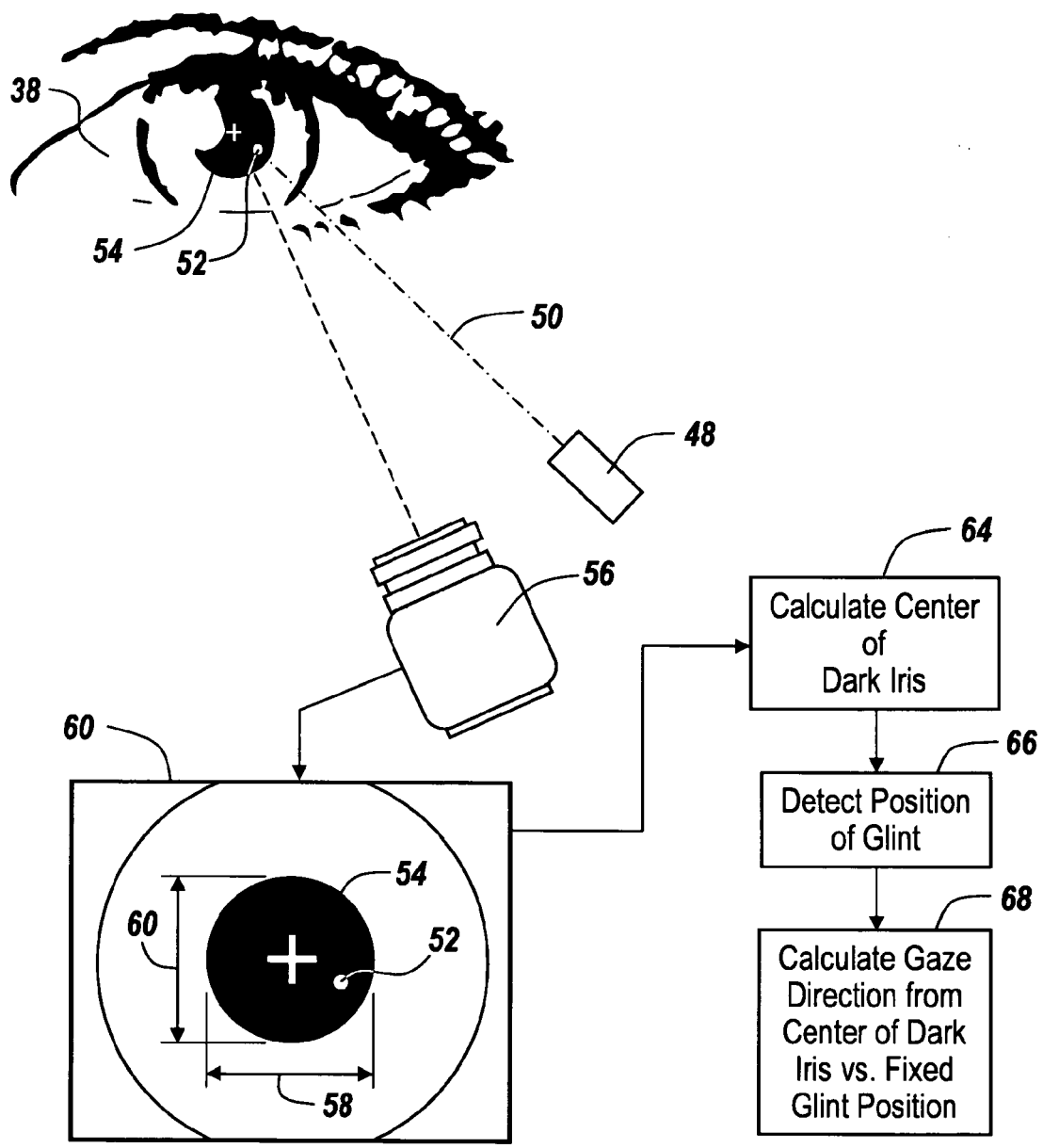
Figure 5:
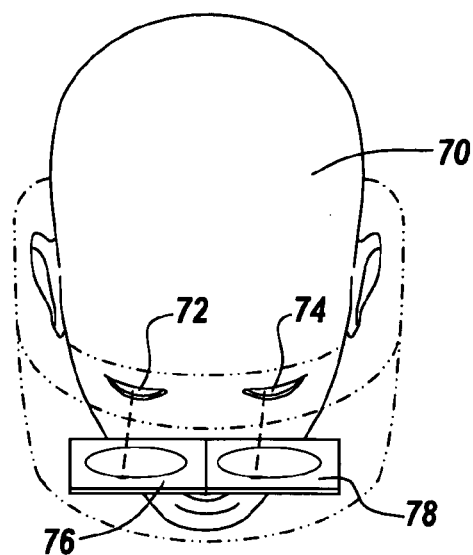
Figure 6:
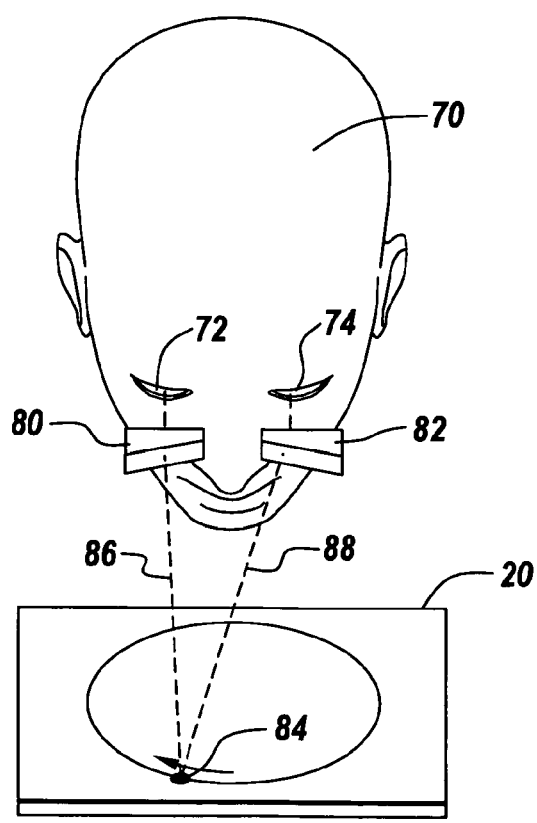
Figure 7:
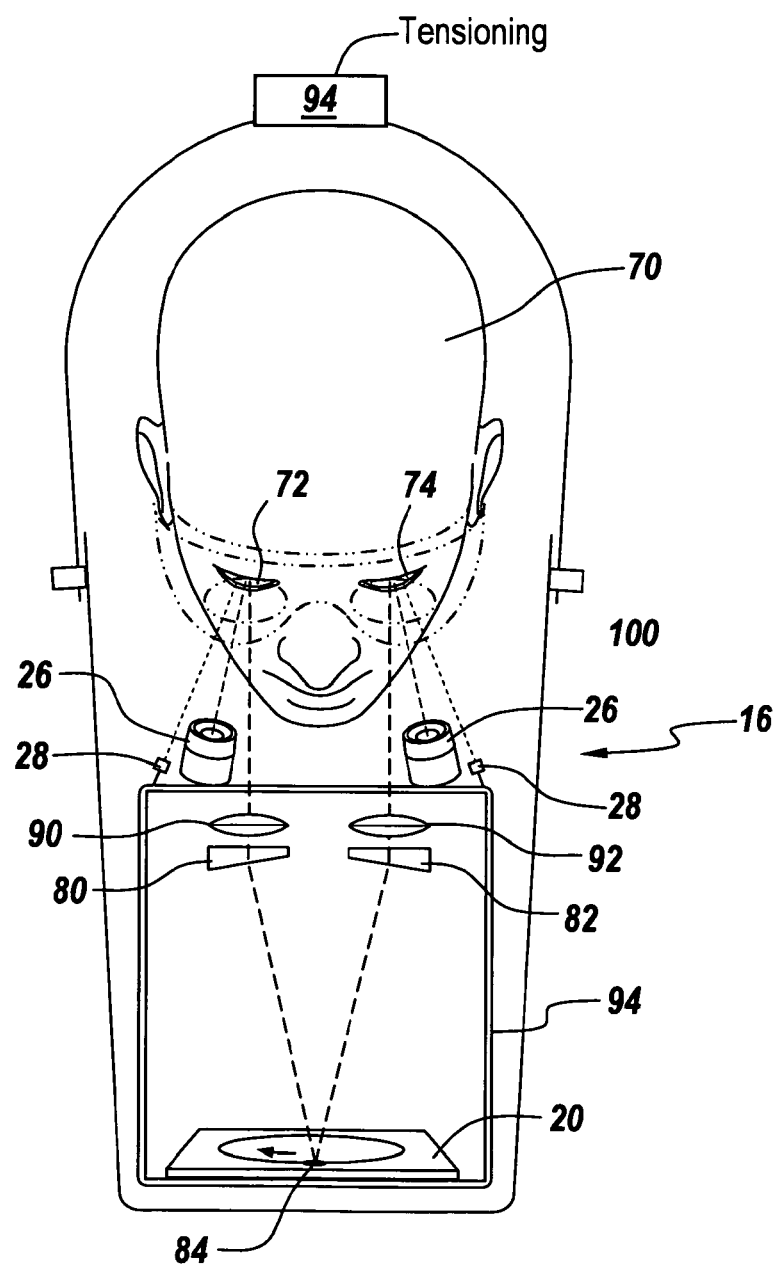
Figure 8:
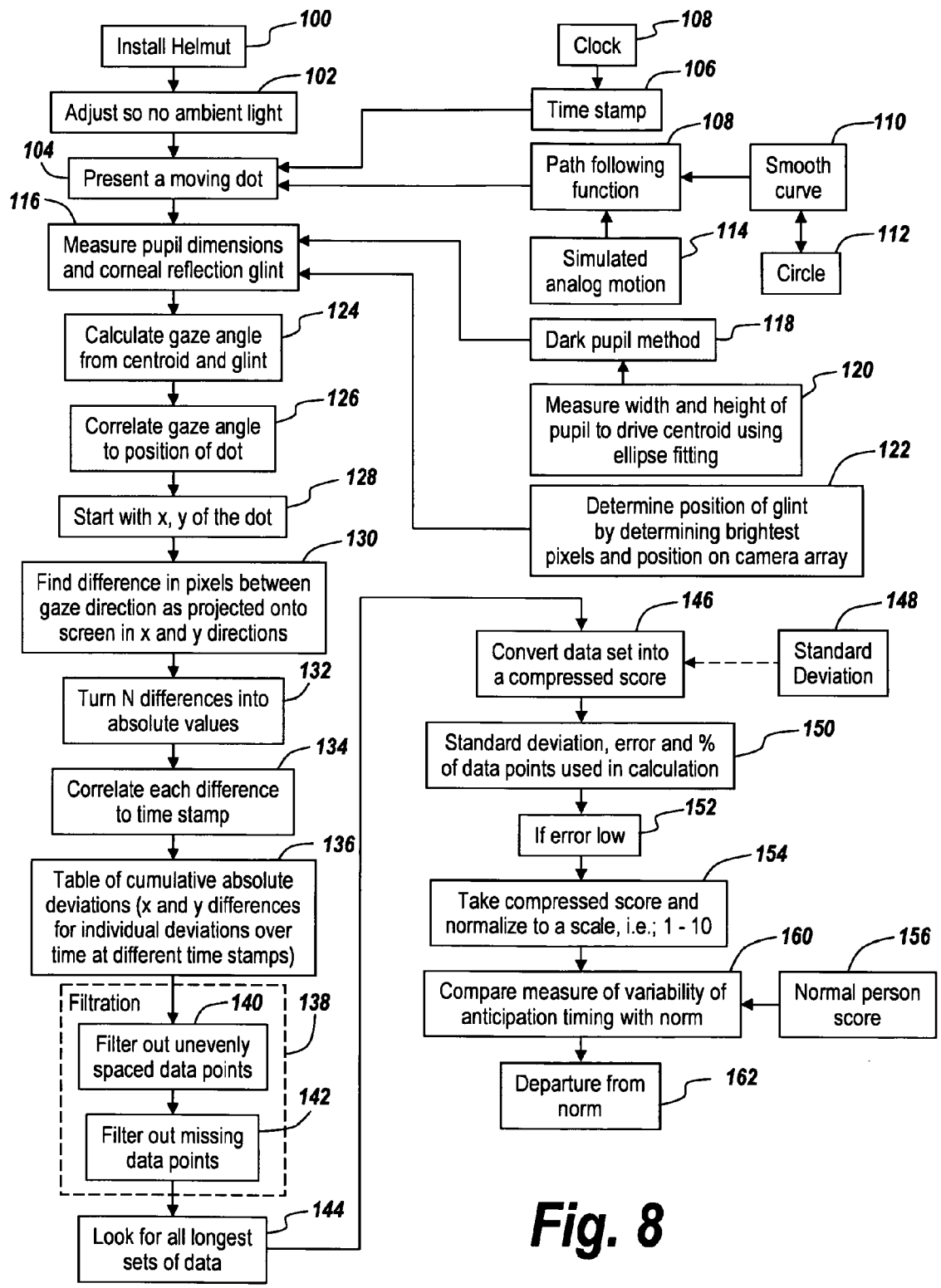
Figure 9:
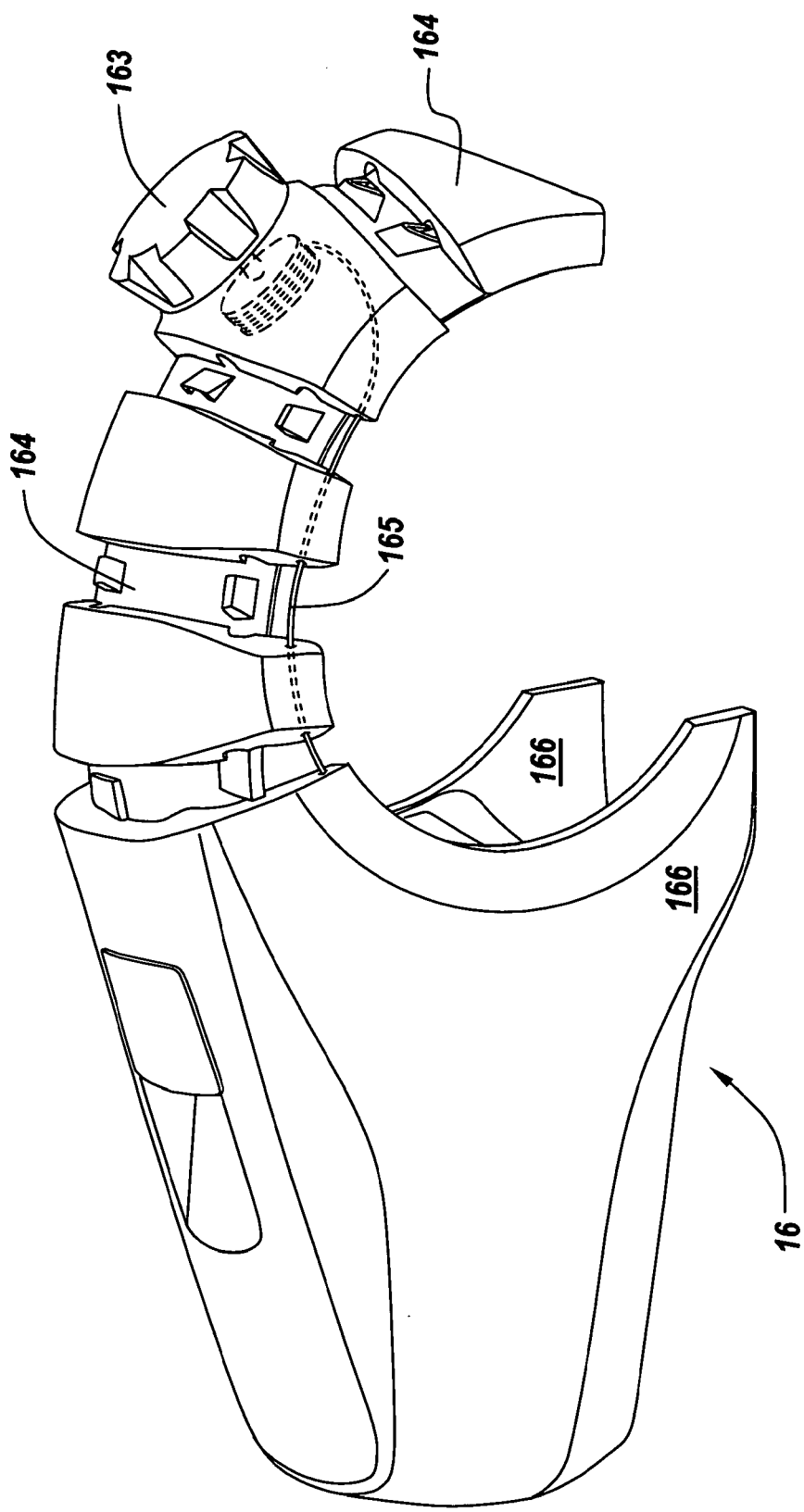
Figure 10:
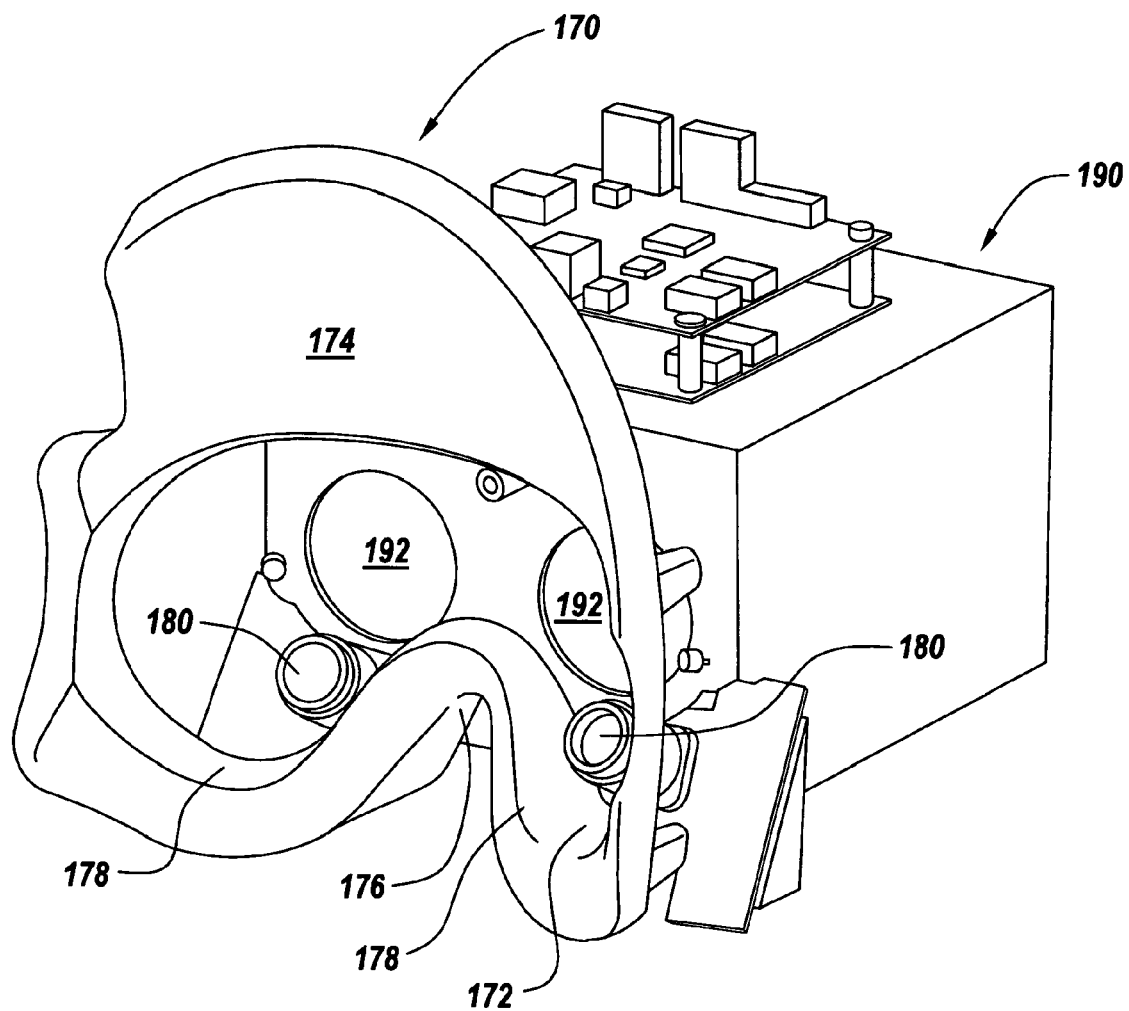

FIG. 4 is a diagrammatic illustration of one method of establishing gaze direction in which an external light source places a dot-like glint on the surface of the eye within the iris and in which a camera is utilized to detect the dark iris and the location of the glint, followed by a calculation of the center of the dark iris and detection of the position of the glint, thereby to permit calculation of gaze direction from the center of the dark iris to the fixed glint position;

FIG. 5 is a diagrammatic illustration of a prior art method of cognitive measurement utilizing a virtual reality headset in which there are two screens, with the individual eyes of the test subject focused on different screens;

FIG. 6 is a diagrammatic illustration of the utilization of prisms to bend the direction at which the eyes are looking so that both eyes focus at a single point on the screen at which the moving dot is presented;

FIG. 7 is a diagrammatic illustration of the utilization of the subject headset including a hood which contains the single screen, prismatic focusing optics, a pair of cameras each individually focused on a different eye, LED light sources one for each eye, and a tensioning mechanism to clamp the headset to the test subject and position the screen at a fixed distance from the individual's eyes, using an internally-carried universal mask;

FIG. 8 is a flow chart showing the processing used to detect variability in the anticipation of the eye as it seeks to track a moving dot; and, FIG. 9 is a diagrammatic illustration of the subject headset in one embodiment showing the structure that surrounds the front portion of an individual's head and an arched spine on which a tensioning device is utilized to clamp the headset onto the test subject; and FIG. 10 is a diagrammatic illustration of the universal mask used in the positioning of the headset to an individual's face, indicating apertures through which the individual's eyes can look, a light source and a pair of cameras which look up at the individual's eyes without being occluded by any portion of the universal mask, also showing the housing utilized to mount the screen in front of the mask.

DETAILED DESCRIPTION OF THE DRAWINGS

Figure 1A:
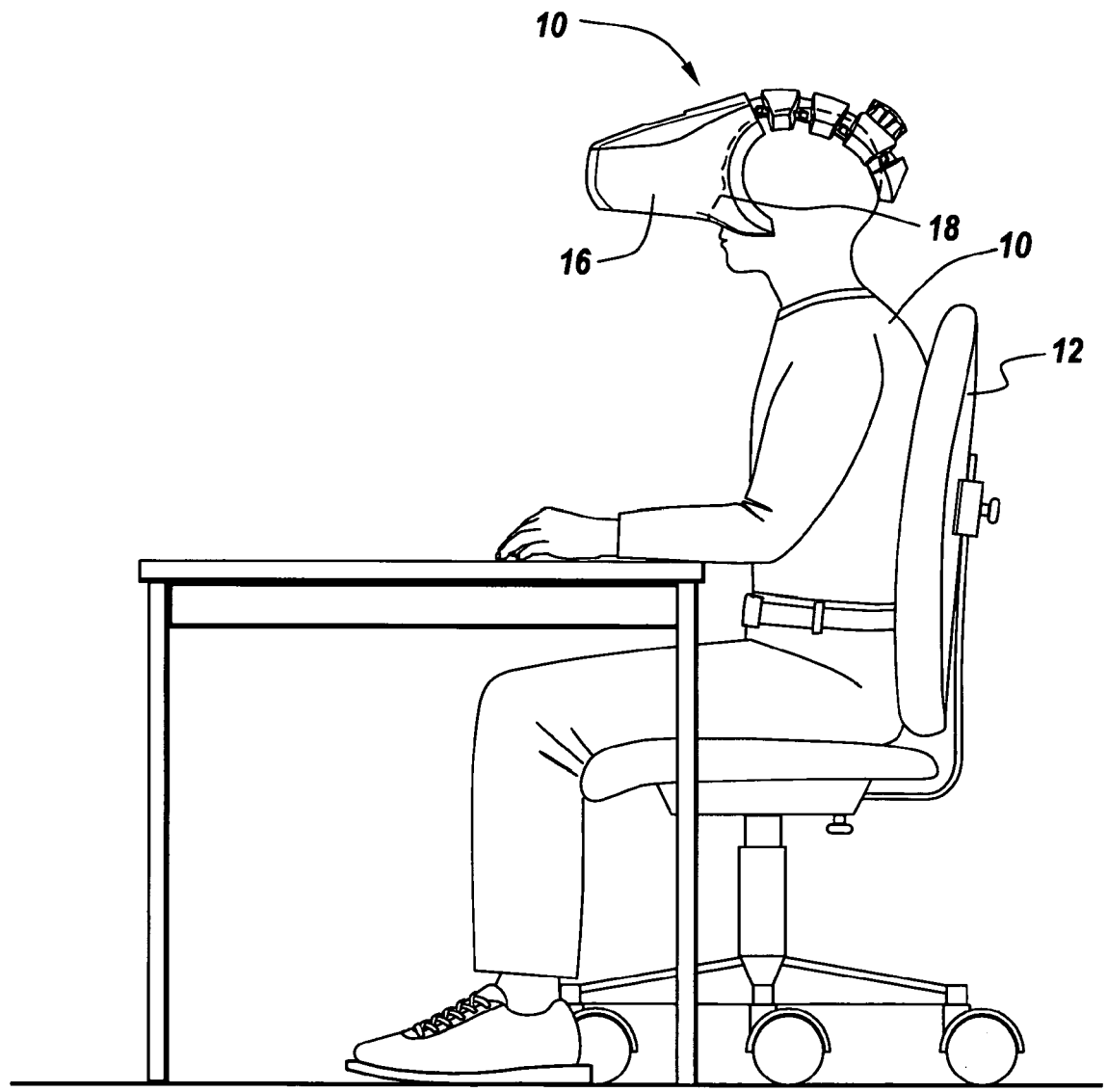
FIG. 1A is a diagrammatic illustration of a test subject provided with a headset that is utilized for psychological testing involving a headset-carried hood positioned in front of the eyes of the test subject.

Referring now to FIG. 1, a test subject 10 is seated in a chair 12 and is provided with a headset which places a hood 16 in front of his face 18. It will be appreciated that this headset is clamped to the head of the individual and places the hood at a fixed position relative to the head such the hood moves with the movement of the individual's head.

It will be appreciated that the hood provides an environmentally closed environment so that outside distractions will not affect the testing procedure.

The headset is a portable device for carrying all of the apparatus that is necessary to track the individual's eyes as he focuses on a moving dot which is presented at a single screen at the forward portion of the hood.

Figure 1B:
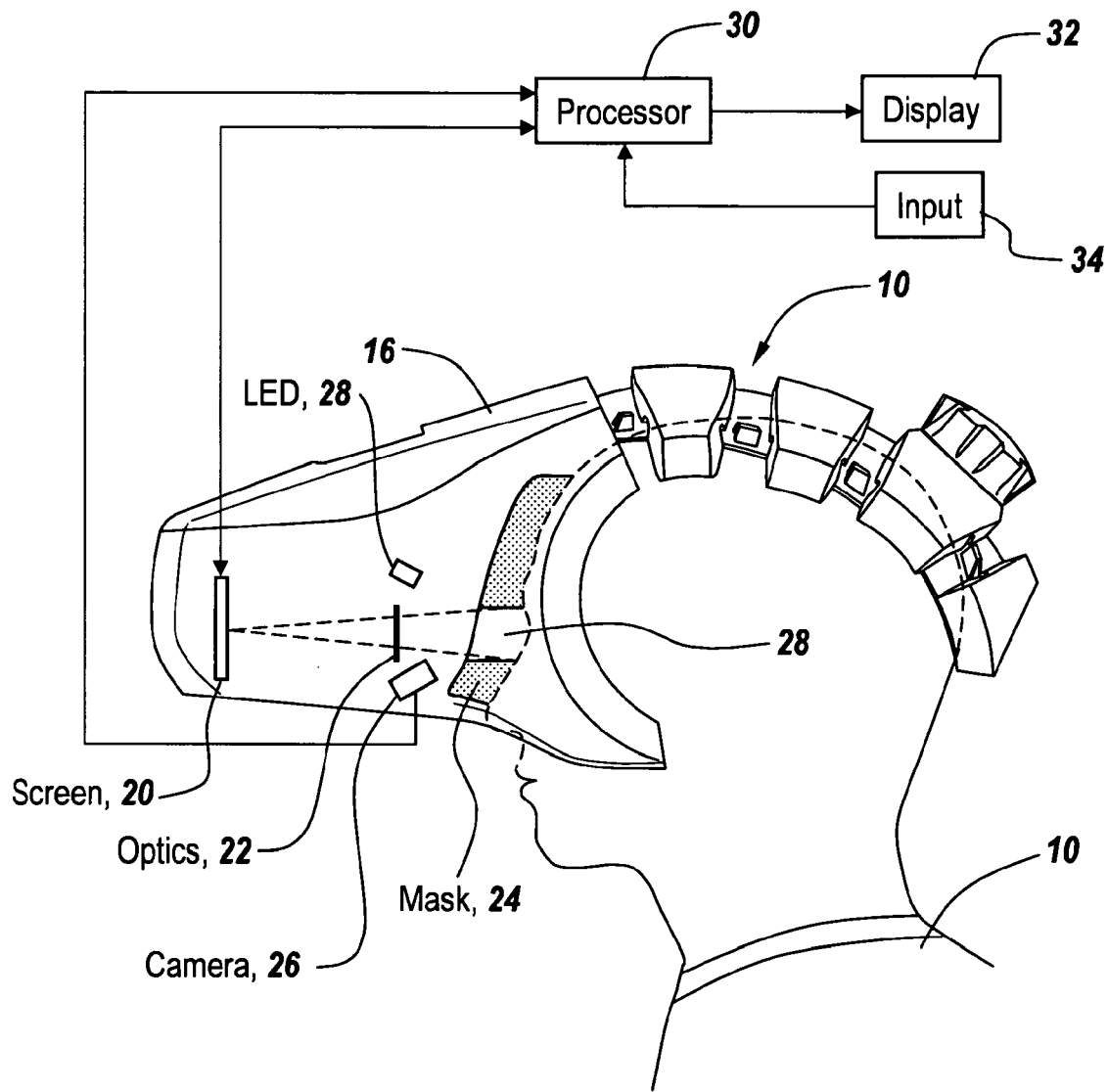
FIG. 1B is a diagrammatic illustration of the hood of FIG. 1A illustrating the components that are located within the headset including a single screen, optics, a camera for each eye, a mask for positioning the headset to the test subject's head and an LED light source for performing the eye tracking that is used in the detection of cognitive ability and brain damage.

Referring to FIG. 1B, what is shown are some of the components that are mounted to the headset, with a screen 20 mounted at the forward end of hood 16 and with focusing optics 22 positioned ahead of a mask 24 that is used to locate the forward portion of the headset at a fixed position relative to the individual's head.

As can be seen, camera 26 is located in the hood underneath an aperture 28 in mask 24 through which the gaze of the individual's eyes passes, and through optics 22 to screen 20. Also light emitting diode sources 28 are located above the test subject's eyes such that a glint is cast on the individual's iris to facilitate gaze tracking.

A processor 30 is coupled to screen 20, camera 26 and other components within the hood, with the processor located within the hood at the upper portion thereof.

The processor is utilized in the measuring of gaze angle as the individual's eyes track a moving dot on screen 20 and provides for a display of the anticipatory timing results at display 32, whereas an input device 34 is coupled to processor 30 to load in data required for the test.

Figure 2:
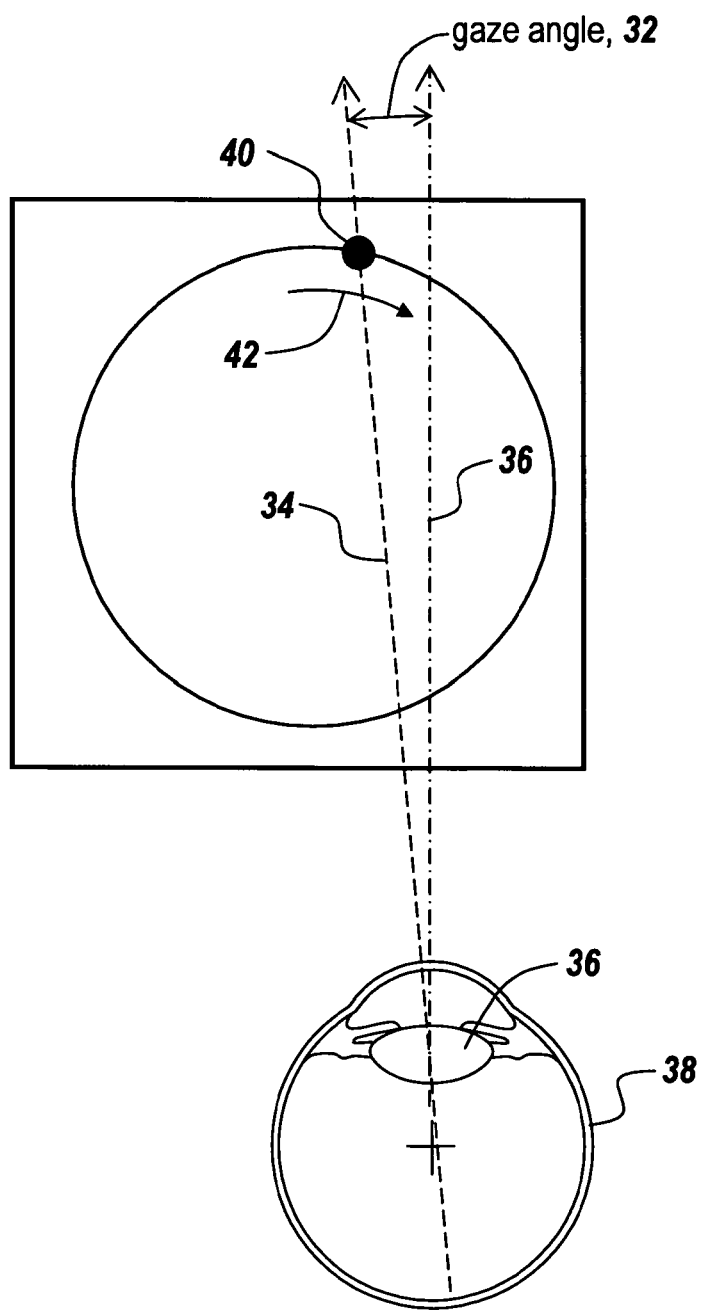
FIG. 2 is a diagrammatic illustration of the utilization of a circularly moving dot to be focused on by an individual's eye in which eye gaze direction is calculated.
Figure 3:
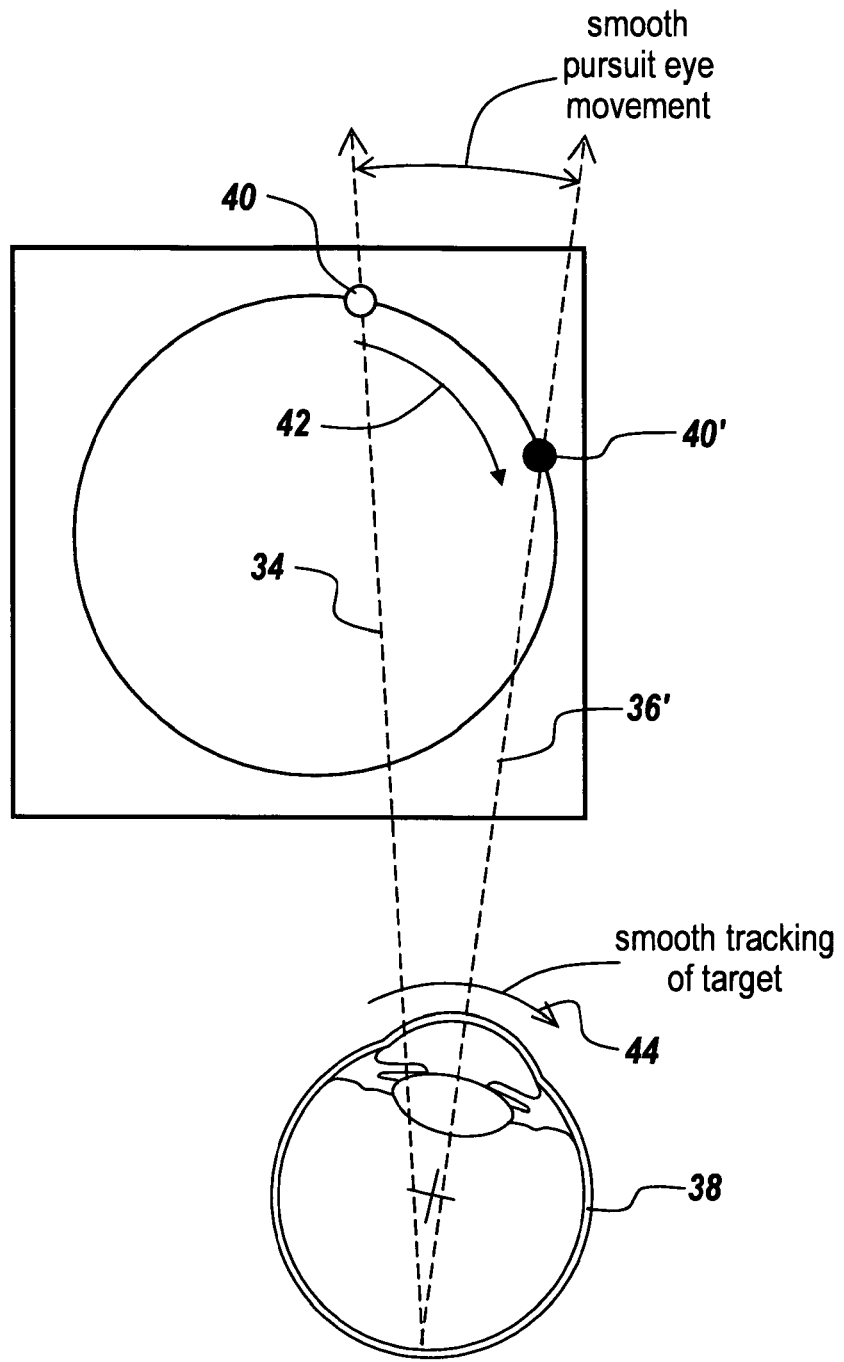
FIG. 3 is a diagrammatic illustration of the movement of the test subject's eye during a smooth pursuit test involving smooth pursuit eye tracking of a dot as it traverses around a circle, showing the difference in gaze direction as an individual attempts to track the moving dot.

Referring to FIGS. 2 and 3, the test that is associated with the subject headset is an eye tracking test which in one embodiment measures gaze angle 32 between a line 34 from the center of lens 36 of eye 38 and line 36 which designates the direction of gaze. As will be discussed, a dot 40 is made a move in the direction of arrow 42 such that as illustrated in FIG. 3 dot 40 moves to a position 40' during the test. Here the angle of gaze is measured from line 34 to line 36' when eye 38 moves as indicated by arrow 44 as the eye tracks the moving dot.

In general the dot presented to the test subject moves in accordance with a function, in one embodiment a Bezier function, to achieve smooth pursuit eye movement (SPEM). It will be appreciated that circular dot movement is a subset of the Bezier function.

The circular movement of the dot is advantageous for the reasons stated hereinbefore so as to eliminate blink responses and responses due to the movement of the dot from left to right or up and down that were problematic in prior eye tracking measurements.

It is the purpose of the subject test to measure the anticipatory timing of the eye as it anticipates the position of the moving dot. With the dot moving in a circle the result is smooth eye pursuit movement, i.e. smooth tracking of the dot by the eye.

While eye tracking utilizing gaze direction measurements has been described hereinbefore, referring to FIG. 4 in one embodiment eye 38 is illuminated with an LED 48 beam 50 to produce a glint 52 on the surface of the eyeball. It will be appreciated that even with the eye moving to track a target, this glint position is stationary.

On the other hand, in one embodiment the dark iris 54 is detected by a camera 56 that is utilized to measure the lateral extent of the dark iris here shown at 58 and the vertical extent of the iris here shown at 60, with the iris periphery presenting an ellipse. With these measurements, the centroid of the ellipsoidal periphery of the iris can be calculated using conventional techniques.

As will be appreciated the image of dark iris 54 is projected by camera 56 onto the cameras' CCD detector array 60, along with glint 52.

With camera 56 trained on the individual's eye it is possible to calculate the center of the dark iris, and the fixed position of the glint, and from this calculation to calculate gaze direction.

In order to do this, processor 30 of FIG. 1B calculates the center of the dark iris at 64 by centroiding techniques, detects the glint position at 66 and calculates the gaze direction from the previously calculated center of the dark iris and the fixed glint position as illustrated at 68 in terms of a vector.

The result is the determination of the gaze direction of one of the test subject's eyes.

While detection of gaze direction is important for one eye, it has been found that it is important to detect the gaze direction of both eyes to be able to select the results from the dominant eye to eliminate the effects of blinking of one or the other of the eyes and because of interocular distance problems when one loses the results of an eye when the eye goes out of view of the camera.

Referring to FIG. 5, in the prior art when attempting to use virtual reality headsets a test subject 70 has his eyes 72 and 74 focused on different stereoscopic screens 76 and 78. The eye tracking measurements made by such virtual reality headsets are problematical first because of the interocular distance between the eyes and secondly because synchronization must be maintained for the images on both screens. Calibration of this system is difficult because the calibration requires correlation between the calibration for one eye versus the calibration for the other eye.

The net result of the above is that it is only with difficulty and much time-consuming calibration that one can determine the gaze direction and therefore the cognitive abilities of the test subject.

Referring to FIG. 6, in the subject system test subject 70 is provided with a pair of prisms 80 and 82 which bend the line of sight of the eyes 72 and 74 such that they focus on display screen 20 at exactly the same point, here illustrated at 84. The bending of the light beams from each of the eyes is illustrated by dotted lines 86 and 88 which converge on dot 84.

Because of the use of the prisms it is unnecessary to take into account interocular distance or calibrate anything having to do with stereoscopic screens.

Thus, in one embodiment the subject invention provides that both of the eyes of the individual taking the test are focused on the same point on screen 20, making measurement of cognitive ability independent of the aforementioned calibration-intense methods of eye tracking.

Referring now to FIG. 7, it can be seen that screen 20 is provided with moving dot 84, also showing the fact that the optical elements involved are not only prisms 80 and 82 but also thin optics 90 and 92 which establish the 40 centimeter distance of the virtual image to correspond to a natural gazing position.

As will be appreciated, hood 16 provides a controlled environment such that ambient conditions are completely removed from the measurement when the headset is in place and the cheeks of the hood are flush with the cheeks of the test taker.

As mentioned before, hood 16 is provided with screen 20, cameras 26 and LED light sources 28, with the optics and the screen being mounted in housing 95 which is carried by hood 16.

As also illustrated, hood 16 is clamped to the face of individual 70 using a tensioning device 94 which assures that the sides of the hood are clamped to side of the test taker's face so that no ambient light leaks in. The tensioning device has a stub which rests just below the occipital lobe of the test taker to securely fix the headset to the test taker's head at a precise location. Thereafter drawing the hood 16 towards the individual's face with the tensioning positions screen 20 a predetermined distance to the test taker's eyes. The hood carrying a universal mask 100 assists in this accurate positioning, with the mask having apertures through which the individual looks toward the screen.

It is the purpose of the universal mask to precisely position the individual's eyes at a predetermined distance from screen 20 which is accomplished when the face of the individual is compressed against the mask, in one embodiment a relatively firm but comfortable material.

As will be discussed, it is the purpose of the mask to be universal insofar as its dimensions and thicknesses accommodate a panoply of different ethnic heads of ranging sizes, while at the same time not getting in the way of cameras 26 which are positioned below the individual's eyes.

In this manner eye gaze measurements can be reliably made in a controlled environment in which the screen is precisely positioned with respect to the eyes of the individual. It is noted that the tensioning device 94 allows for quick mounting and dismounting of the headset.

In operation and referring now to FIG. 8, as seen at 100 the headset is installed on the head of a test subject. The headset is adjusted through the aforementioned tensioning so that no ambient light is available inside the hood as shown at 102.

The test subject is then presented with a moving dot as illustrated at 104, with the dot having a time stamp 106 associated with it and with the time stamp being driven by system clock 105. The path of the dot is driven in accordance with a path following function as illustrated at 108 to cause the dot, in one embodiment to follow a smooth curve 110, of which a circle 112 is a subset.

Path following function 108 simulates analog motion as illustrated at 114 such that as the moving dot moves about a curve, it represents smooth so that the movement of the dot simulates analog motion.

In order to determine gaze direction the system measures the pupil dimensions and the corneal reflection glint position as illustrated at 116. In order to measure the pupil dimensions the system utilizes the dark pupil method 118, which operates by measuring the width and height of the pupil to derive a centroid using an ellipse fitting algorithm as illustrated at 120.

As illustrated at 122, the position of the glint is determined by determining the brightest pixels and finding the location of the brightest pixels on the camera sensor array.

Having determined the center or centroid of the dark pupil and the position of the glint, as illustrated at 124, the gaze angle is calculated by the vector from the centroid to the glint.

This measurement of the distance between the centroid and the glint permits calculating the gaze angle which is correlated to the position of the dot as illustrated at 126 starting with the x and y coordinates of dot 128, followed by finding the difference in pixels between the gaze direction as projected onto the camera sensor array in the x and y directions as illustrated at 130.

These differences in the x and y direction are turned into absolute values as illustrated at 132 which are then correlated with the time stamps as illustrated at 134 such a table is created which lists the absolute values and the associated time stamp. The distance value at the time stamp correlates to the length of time it takes for the eye to track the dot at the particular time stamp time. There is thus a correlation between each absolute difference value and the associated time stamp.

More particularly, and as illustrated at 136 the correlated differences with time stamps are used to populate a table of cumulative variations which are the x and y differences over time at different time stamps. The table is then used to calculate absolute deviations that instantiates the motion of the eye as it tracks the dot and provides a metric of anticipation timing, meaning the time between the movement of the dot and the movement of the eye tracking the dot. This is compressed using standard deviation techniques in one embodiment.

As can see by dotted box 138 various artifacts are filtered out from the table of cumulative absolute deviations, the first being the filtering out of unevenly spaced data points as shown at 140. During the course of the measurement it is oftentimes true that data points can be dropped or lost and therefore the data representing smooth eye tracking has some unevenness. By filtering out unevenly spaced data points this problem is solved.

The second part of the filtration as shown at 142 relates to filtering out of missing data points as opposed to the unevenly spaced data points. If during the tests there are periods of time when data is unavailable as for instance during blinking and the like, these points are filtered out of the stream of data from the cumulative absolute deviations table.

After the filtering, the system looks for all longest sets of data as illustrated at 144. Thus the most accurate data is that which is attributed to a long continuous set of data representing the smooth eye pursuit measurements. Taking the longest sets of data increases the reliability of the measurement.

Then the system as illustrated at 146 converts the data set into a compressed score, in one embodiment utilizing standard deviation techniques as illustrated at 148.

Thereafter the standard deviation, error and percentage of data points used in the calculation is calculated at 150 and if the error is low as illustrated at 152 the compressed score is taken and normalized to a scale, for instance a scale of 1 to 10 as shown at 154.

This score is then compared at 156 with a score from a normal test subject, with the departure from the norm detecting cognitive impairment as illustrated at 162.

Thus in one embodiment the compressed scores are compared to a scoring baseline for instance for normal individuals so that the relative cognitive ability of the test subject can be ascertained.

Note if the subject anticipates the dot with a high variability, this is a measurement of impairment. High variability in anticipatory timing is primarily due to the fact that the test subject is jumping ahead and waits for the dot to catch up.

The jumping ahead and waiting can be a result of any number of different cognitive disabilities originating from various different circuit paths through the brain through which visual cues pass and, or through which eye muscle signals must pass to move the eye. It can be shown that the path through the brain from the detection of the moving the dot to the active tracking of the dot with one's eyes is quite long and includes many brain functions. This is because the path passes through the frontal lobe, then to the back of the brain to the anterior lobe, and then back again to the front of the brain to the motor cortex for eye movement control. This long path length is critical in understanding that any impairment along the length of this path will be represented by a high variability in the smooth eye pursuit tracking of the eye from one dot position to the next and is a sensitive measure of overall cognitive performance. It has been found that one or more variability metrics in anticipation timing can be traced to a specific type of brain impairment. Thus the ability to reliably measure variabilities in anticipation timing offers a powerful tool in detecting brain damage and cognitive impairment.

It will be appreciated that the anticipation timing for a normal subject can establish a baseline against which a test subject is compared. When using such a baseline one can very rapidly assess the overall cognitive ability of a test subject by comparing the compressed score to a normalized baseline.

Thus, the subject technique measures the variability in anticipation timing and does so in a way that filters out or disregards artifacts and eliminates any environmental effects; or for that matter any effects that are associated with stereoscopic systems. The measurement of the departure of the variability of anticipation timing from the norm is shown at 162, and it is this measure of variability that is a sensitive measure of overall cognitive impairment, given a compressed score norm to which the compressed score measurement is compared.

As shown in FIG. 9 hood 16 of the headset is easily mounted on the head of a test subject by a tensioning system including a tensioning knob 163 that is used to urge the occipital lobe contact pad 164 towards hood 16 by pulling hood 16 back over spine 167 which is flexible. This is accomplished by tensioning wires 165 to either side of spine 167 towards the spine and compress hood 16, its mask and cheek plates 166 to the face of the test subject. Note that the headset is easily released with a turn of knob 163.

Referring now to FIG. 10 what is shown is a representation of the mask here shown at 170, which has a number of features that make it universal and capable of fitting to any adult face, regardless of ethnicity or gender to provide a fixed distance between the eyes and the screen, or the eyes and the LED light sources used to provide the glints.

First, the mask is made from a compound foam 172 that is non-compressible, yet comfortable. In one embodiment the foam is a polyurethane foam model PG 250 made by Spectrum Plastics Group of Westminster Colo., with the foam having a 55 shore hardness. The shape of the mask was designed by taking an average of reported face measurements across the population demographic in the 90% percentile between the ages of 8 and 20, and thus allows for a universal fit.

Secondly, the curvature of the forehead-contacting portion 174 of mask 170 has a horizontal curvature of a radius of 79 mm at the bottom, closer to the eyes, and narrows to the top of the forehead of the mask, with a vertical curvature of a radius of 107 mm. The forehead-contacting portion 174 of mask 170 is 165 mm wide at the bottom and 155 mm wide at the top with such measurements used to accommodate a wide variety of forehead widths and shapes.

Thirdly, the nose cutout 176 has a nose depth of 60 mm and nose width of 90 mm, designed to accommodate even the longest and widest of noses.

Finally, the portion of the mask 178 that engages the cheekbones was sized to give the IR LEDs 180 enough depth in front of the eyes. Note that the cheekbone of the mask refers to a narrow horizontal cheekbone plate.

The above establishes a predetermined distance between the LEDs and respective eyeballs so that this distance is the same for all faces. The result is a glint that is as small and consistent as possible, from one test subject for the next.

The mask when properly configured properly contacts the forehead and the cheekbones and creates a light tight barrier to outside light so that the mask surrounds the face with a light-tight seal. The curvature of the mask horizontally across the eye portion has a radius of 277 mm and a width of 200 mm, which assists with this light-tight seal.

It has been shown that the subject test can be administered in less than three minutes and that the compressed score is valid without the utilization of time consuming calibration techniques due to the complete control over environmental factors, as well as the ability to provide a headset with a single screen that presents a dot on which both eyes simultaneously focus.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. An apparatus comprising:
a headset adapted to fit over a face of a test subject and to be mounted on a head of the test subject, the headset including
a single screen positioned at a predetermined distance from the eyes of the test subject when the headset is mounted on the head of the test subject,
a pair of lenses, including a lens positioned between each eye of the test subject and the screen, to focus light emitted from the screen onto the eyes of the test subject; and
a camera located within the headset and configured to be trained on an eye of the test subject to facilitate determination of gaze direction by the test subject.

2. The apparatus of claim 1, wherein the headset includes a hood carrying the screen at one end of the hood, and side panels adapted to block outside light from entering the hood when the headset is mounted on the head of the test subject.

3. The apparatus of claim 1, wherein the headset further includes one or more light sources for illuminating an eye of the test subject, and wherein the camera is for detecting reflections of the one or more light sources, reflected by the eye of the subject, and the pupil of the eye of the test subject.

4. The apparatus of claim 3, wherein the headset includes a headset-mounting system for mounting the headset on the head of the test subject and fixing the screen with respect to the eyes of the test subject.

5. The apparatus of claim 3, wherein the one or more light sources are one or more infrared light sources.

6. The apparatus of claim 3, wherein the one or more light sources are one or more infrared light sources and the camera is an infrared camera that captures reflections of infrared light, reflected by the eye of the subject.

7. The apparatus of claim 6, wherein the one or more light sources are one or more infrared light emitting diodes.

8. The apparatus of claim 6, wherein the camera is positioned off-axis from a line of sight of the test subject.

9. The apparatus of claim 1, wherein the headset includes a headset-mounting system for mounting the headset on the head of the test subject and fixing the screen with respect to the eyes of the test subject.

10. The apparatus of claim 1, further configured to present an object moving along a path on said screen, the moving object associated with a time stamp driven by a system clock.

11. The apparatus of claim 10, wherein the headset includes or is connected to a processor that calculates gaze direction and measures anticipatory timing of the movement of the eyes of said test subject as it tracks said moving object from said calculated gaze direction.

12. The apparatus of claim 11, wherein said processor calculates variability in anticipatory timing as the eyes of said test subject track the moving object from one position to the next on said screen.

13. The apparatus of claim 12, wherein said moving object moves on a path in equal timed increments.

14. The apparatus of claim 11, wherein the measured anticipatory timing is compared with anticipatory timing of a normal test subject, and wherein a difference between the measured anticipatory timing and the anticipatory timing associated with the normal test subject indicates cognitive impairment of the test subject.

15. The apparatus of claim 11, further configured to measure variability in the anticipatory timing as the moving object moves from one position to the next on said path, the anticipatory timing including a period of time taken for the eyes of the test subject to direct gaze to the moving object.

16. The apparatus of claim 15, wherein said period of time is lead time or lag time.

* * * * *

UNITED STATES PATENT AND TRADEMARK OFFICE
CERTIFICATE OF CORRECTION

PATENT NO. : 9,439,592 B2  
APPLICATION NO. : 14/685473  
DATED : September 13, 2016  
INVENTOR(S) : Stack et al.

It is certified that error appears in the above-identified patent and that said Letters Patent is hereby corrected as shown below:

In the claims,

Claim 1, column 16, line 20, please delete "be trained on an eye" and insert --capture images of an eye--.

Signed and Sealed this
Twenty-ninth Day of November, 2016

Michelle K. Lee
*Director of the United States Patent and Trademark Office*